(12) United States Patent
Förster

(10) Patent No.: US 7,717,706 B2
(45) Date of Patent: May 18, 2010

(54) SELF-LIGATING BRACKET AND USE THEREOF IN ORTHODONTICS

(76) Inventor: Rolf Förster, Vogesenallee 58, Pforzheim (DE) D-75173

( * ) Notice: Subject to any disclaimer, the term of this patent is extended or adjusted under 35 U.S.C. 154(b) by 142 days.

(21) Appl. No.: 11/807,307

(22) Filed: May 25, 2007

(65) Prior Publication Data
US 2007/0281269 A1 Dec. 6, 2007

(30) Foreign Application Priority Data
Jun. 2, 2006 (DE) ........................ 10 2006 027 130

(51) Int. Cl.
*A61C 3/00* (2006.01)
(52) U.S. Cl. .......................... 433/11; 433/14
(58) Field of Classification Search ................ 433/8, 433/10, 11, 13, 14, 17
See application file for complete search history.

(56) References Cited

U.S. PATENT DOCUMENTS

| 5,586,882 A * | 12/1996 | Hanson | ................... 433/13 |
| 6,368,105 B1 * | 4/2002 | Voudouris et al. | ............ 433/11 |
| 2006/0110699 A1 | 5/2006 | Förster | |

FOREIGN PATENT DOCUMENTS

DE 20 2004 017 951 U1 5/2005

* cited by examiner

*Primary Examiner*—Ralph A Lewis
*Assistant Examiner*—Eric Rosen

(57) ABSTRACT

The self-ligating bracket with base;
base support;
occlusal and gingival wall with ligature wing from support;
slot separating the walls,
passage extending through support in gingival-to-occlusal direction;
and resilient clip with mutually connected labial and lingual legs;
lingual leg received and arranged for displacement in passage in gingival-to-occlusal direction, between closed and open position of clip;
in closed position, labial leg extends into cutout in gingival or occlusal wall, with stop for labial leg;
in open position, tip of labial leg positioned above the occlusal or gingival wall, labial leg of clip provided with wing extending in distal and/or medial direction;
in closed position of clip, one wing is positioned above the slot,
lingual extension of labial leg of clip is positioned in cutout, with extension narrower than width of labial leg;
extension of labial leg of clip contacts the closed position, with the labial stop even when slot is empty.

30 Claims, 12 Drawing Sheets

SELF-LIGATING BRACKET AND USE THEREOF IN ORTHODONTICS

The present invention relates to a self-ligating bracket for use in orthodontics having a base;

a support arranged on the base;

an occlusal wall with at least one occlusal ligature wing extending from the support;

a gingival wall with at least one gingival ligature wing extending from the support;

a slot separating the occlusal wall and the gingival wall one from the other and extending continuously in the mesial-to-distal direction;

a passage which extends through the support in the gingival-to-occlusal direction; and a resilient clip having a labial leg and a lingual leg that are connected one to the other by an occlusal section;

the lingual leg being received in the slot and being arranged for displacement in the slot in the gingival-to-occlusal direction between a closed position in which the labial leg extends into a cutout in the gingival wall and an open position of the clip in which the tip of the labial leg is located above the occlusal wall.

As the clip is moved from its open position into its closed position, the labial leg springs into the slot, and its tip comes to rest at an initial stress against a lingual stop that forms a lingual boundary of the cutout in the gingival wall of the bracket. Such a bracket has been known from DE 20 2004 017 952 U.

The resilient clip of the known bracket is narrower than the length of the slot. The labial leg of the clip is provided with two wings which extend one in distal direction and the other one in mesial direction and which come to lie in the slot when the clip occupies its closed position. When an arch wire of rectangular cross-section is introduced into the slot, which has a height greater than the clear width available below the labial leg of the clip—and this is regularly the case—then the labial leg of the clip is lifted, against the effect of its elastic restoring force, up to a maximum height in which it abuts against a bridge connecting the two gingival ligature wings and forming a labial boundary of the cutout in the gingival wall of the bracket.

Although the restoring force exerted on the arch wire by the clip may in certain individual cases actually increase the correction force exerted on a misaligned tooth, the restoring force, having a significant value of some Newton, will in any case increase friction between the arch wire and the slot in the bracket and will as a rule slow down the progress in the process of correction of the misalignment.

Now, it is the object of the present invention to remedy that disadvantage and to extend the potential applications of brackets of the before-mentioned kind.

That object is achieved by a bracket having the features defined in Claims 1 and 2, by application of such brackets to the correction of misalignments of teeth so important that an arch wire accommodated in the slot will resiliently deflect at least one wing in the labial direction during the correction process, and by a kit having the features defined in Claim 23. Advantageous further developments of the invention are the subject-matter of the sub-claims.

In the brackets according to Claim 1, the position of the resilient clip in its closed position and in unloaded condition is such that the labial leg has a greater distance from the bottom of the slot, from the very beginning, than would be the case with the known self-ligating bracket. Preferably, the clip used in the bracket is sufficiently wide in the unloaded condition so that the labial leg of the clip will not exert any pressure on any of the arch wires encountered in orthodontic practice as long as they extend in the slot rectilinearly. The largest cross-sections of orthodontic arch wires encountered in practice are 0.022 inches×0.025 inches, 0.025 inches being the height the arch wire can occupy above the bottom of the slot in the bracket. 0.025 inches correspond to 0.64 mm. So long as the arch wire, having been mounted on the teeth to be corrected, is not bent in labial direction so far that it comes into contact with the labial leg of the clip, the clip will not exert any force on the arch wire, but will only act to secure it in its position. In that case, no frictional grip and no sliding friction that could slow down the progress of the treatment will develop between the arch wire and the clip.

However, in cases where an extreme misalignment of teeth is to be corrected, it may happen that the arch wire may get deflected in labial direction on one side or on both sides of the bracket to such an extent that it may exert pressure on the labial leg of the clip on one side or on both sides. If the labial leg of the clip is not in contact from the very beginning with the labial stop that delimits the cutout in the gingival or the occlusal wall of the bracket in the labial direction, then the labial leg of the clip is first slightly raised until it abuts against the labial stop whereafter—depending on the form of the arch wire—at least one of the wings of the labial leg of the clip is resiliently deflected in the labial direction. Surprisingly, this instead of slowing down the process of correction of the misalignment of the tooth, rather acts to accelerate that process quite considerably. Corrections of extreme misalignments, for which such acceleration could be observed, include displacing a tooth from a lingually shifted initial position to its normal position, rotating a tooth, moving forward and rotating a tooth into a gap in a row of teeth left by extraction of a disturbing tooth.

In a bracket according to the invention, the clip—except for the wings—is preferably positioned between two pairs of ligature wings. The width of the dip is insofar smaller than the length of the slot. The at least one wing provided on the labial leg of the clip constitutes a local enlargement of the clip. Preferably, there are provided two wings, one extending in distal direction and the other one extending in mesial direction. The wings are located above the slot, delimiting it in labial direction, when the clip is in its closed position. Preferably, the wings do not extend beyond the ends of the slot.

A cutout in the gingival or the occlusal wall of the bracket delimits the clearance of motion of the labial leg of the clip in lingual-to-labial direction. The cutout has a length smaller than the length of the slot, and preferably also smaller than the width of the clip, measured across the wings, and preferably not greater than the spacing between the two gingival or occlusal bracket wings. The gingival or occlusal extension of the labial legs of the clip projects into the cutout. The length of the cutout in the gingival or occlusal wall of the bracket preferably is only slightly greater than the width of the extension of the labial leg of the clip. All in all, the position of the extension of the labial leg in the closed position of the clip is tightly defined even under load by an arch wire.

The wings are, however, not subject to those narrow limits; they can be resiliently deflected under the effect of an arch wire, adapting themselves closely to that arch wire without the edge of the wings being pressed into the arch wire. To further reduce friction, the edge of the wings preferably is rounded. Further it is preferred to design the wings in such a way that their width diminishes toward their tips so that they can be bent most easily at their tips, which assists in adapting the wings to the arch wire in a favorable way, smoothly and at low friction.

A most simple design of the clip is obtained when both wings extend in parallel to the bottom of the slot. A further reduction of friction is achieved according to a further development of the invention where the wings are curved in labial direction from the very beginning. Friction between the wings and an arch wire can further be reduced by giving the wings a configuration such that they will oppose lesser resistance to bending in labial direction than the main part of the clip from which the wings start out. This can be achieved in various ways, for example by making the wings thinner than the main portion of the clip. This can be realized, for example, in that the wings are pressed to give them a thinner shape as they are punched out from a strip-like semi-finished product. Another method consists in ensuring that the material from which the clip is formed is softer in the area of the wings than in the area of the main portion of the clip. Starting out from a strip-like semi-finished product from which the clips can be produced by punching and bending, the strip-like semi-finished product can be annealed in the marginal area from which the wings are to be formed. Another possibility consists in weakening the material between the wings and the main portion of the clip, for example by grooves, cutouts or a perforation, which may be formed in a single operation as the clip is punched out from the semi-finished product. The cited measures, which cause the wings to oppose lesser resistance to bending in labial direction than the main portion of the clip, may be used each individually or in combination.

In the closed position of the clip, the wings should be positioned above the slot or in the upper region of the slot. At the point where the wings foot on the main portion of the clip, they may also partly project into the cutout where the extension of the labial leg of the clip is located. Preferably, however, the wings will not extend into that cutout in the gingival or the occlusal wall of the bracket.

The action of the arch wire may not only cause the wings of the clip to be bent, but may also exert a torsional load on the labial leg of the clip. This is true especially in cases where the arch wire acts on one wing only or—if two wings are provided—where the arch wire acts on the one wing more strongly than on the other wing. The resistance opposed to any torsional strain by the labial leg of the clip depends not only on the shape and the elastic properties of the material from which the clip is made, but also on the shape of the cutout in the gingival or the occlusal wall of the bracket in which the extension of the clip is located in its closed position.

The resistance opposed to any torsional strain by the labial leg of the clip may be reduced with advantage by an arrangement where the labial edge of the cutout, forming a labial stop for the extension of the labial leg of the clip in its closed position, does not extend rectilinearly and in parallel to the bottom of the slot, as in the prior ort, but projects in lingual direction in the region between a distal edge and a mesial edge of the cutout. This means that the labial edge of the cutout is retracted and/or set back from the tip of the projection in labial direction, between the tip of the projection and the distal edge of the cutout on the one side and the mesial edge of the cutout on the other side. Compared with the tip of the projection, the labial edge of the cutout preferably is set back the farthest in the region immediately before its distal and mesial edges. Although a single such projection will be sufficient, a plurality of projections arranged in a row may be provided as well. The one or more projections have the effect that the extension of the labial leg of the clip comes to abut against one or—in some cases—against several such extensions and can evade any torsional strain encountered more easily because either the distal edge or the mesial edge of the extension of the clip can be rotated into the space present before the retracted labial edge of the cutout.

This is an advantage not only for a bracket with a clip whose labial edge is in contact with the labial edge of the cutout from the very beginning, but also for brackets where the labial leg of the clip in its initial position abuts, or occupies a position slightly before abutting, against the lingual edge of the cutout.

The labial edge of the cutout in the gingival and/or the occlusal wall of the bracket is set back in lingual direction, preferably mirror-symmetrically relative to its center plane that crosses the slot. This facilitates radial movement of the labial leg of a clip, having one wing extending in distal direction and one wing extending in mesial direction, both in distal direction or in mesial direction. If the clip used comprises one wing only, which extends in distal direction or in mesial direction, rotational movements in distal or in mesial direction, respectively, are correspondingly facilitated, it being understood that in that case the type of clip to be used can be selected depending on the nature of the misalignment of the respected tooth that is to be corrected.

Preferably, the central portion of the labial edge of the cutout projects the farthest in lingual direction. In this case, the labial leg of the clip can be rotated on such a projection in the way of a rocker in the one or the other direction, depending on the particular application. Such a centrally arranged projection may be formed, for example, by giving the labial edge of the cutout a convex shape. When subjected to torsional strain, the labial leg of the clip can then roll on the convex edge of the cutout over a certain angle.

Another approach consists in selecting the shape of the labial edge of the cutout so that two straight sections are provided that extend at an angle of more than 180° one relative to the other. The two straight sections may in this case extend from a common, preferably centrally arranged angle point on which the labial leg can be supported and will be allowed to tilt to the one or the other side, depending on the direction of torsion strain, until it gets into contact with the straight section toward which it is inclined, whereupon the resistance to any further torsional strain will clearly increase.

However, instead of providing that such straight sections which, extending at an angle of more than 180° one relative to the other, project from a common angle point, there is also the possibility to provide an additional third straight section which preferably extends in parallel to the bottom of the slot. In that case, provided reasonably symmetrical strain is exerted by the arch wire, the labial leg will encounter a solid contact surface which advantageously facilitates translation of a tooth.

Preferably, the width of the extension of the labial leg of the clip and the dimensions of the cutout engaged by the extension are mutually adapted so that the labial leg will not get permanently distorted by the arch wire in the course of an orthodontic treatment.

Another advantage of the invention lies in the fact that the bracket can be used together with clips of different shape that can be exchanged one against the other. In addition to a bracket that can be used without a clip, a kit according to the invention therefore contains at least two clips that distinguish themselves one from the other in that in the closed position of the first clip its labial leg is in contact with the labial stop or will come to lie near the stop that delimits the cutout in the gingival wall of the bracket in labial direction. The second clip is of a kind known in the art which, in its closed position, has its labial leg in contact or nearly in contact with the lingual stop that delimits the cutout in the gingival wall of the bracket in lingual direction, without any action of an arch wire.

Such kit makes it possible for an orthodontist to cover more applications at especially low cost than has been possible before.

Further features and advantages of the invention can be derived from the description that follows of one preferred embodiment illustrated in the drawing in which.

The bracket is provided with a curved base 1 the curvature of which is approximated to the front of a tooth. The bottom surface 2 of the base 1, which forms the lingual side of the bracket, is provided with undercut projections 3 arranged in series. The projections 3 are rhomb-shaped in the cross-section shown in FIGS. 3 and 4, and are rectangular in a cross-section taken in parallel to the bottom surface 2. In order to bond the bracket onto a front of a tooth, an adhesive may be applied on the bottom surface 2. Interleaving between the projections 3 and the adhesive provides good bonding strength. The projections 3 and, together with them, the undercuts are orientated identically in each row. Between the rows they are, however, alternately oriented in one and the other direction. This has the effect that when thrust is applied on the bracket in the gingival-to-occlusal direction the same bonding strength will be achieved as in the case of a force acting in the occlusal-to-gingival direction.

Figure 1:
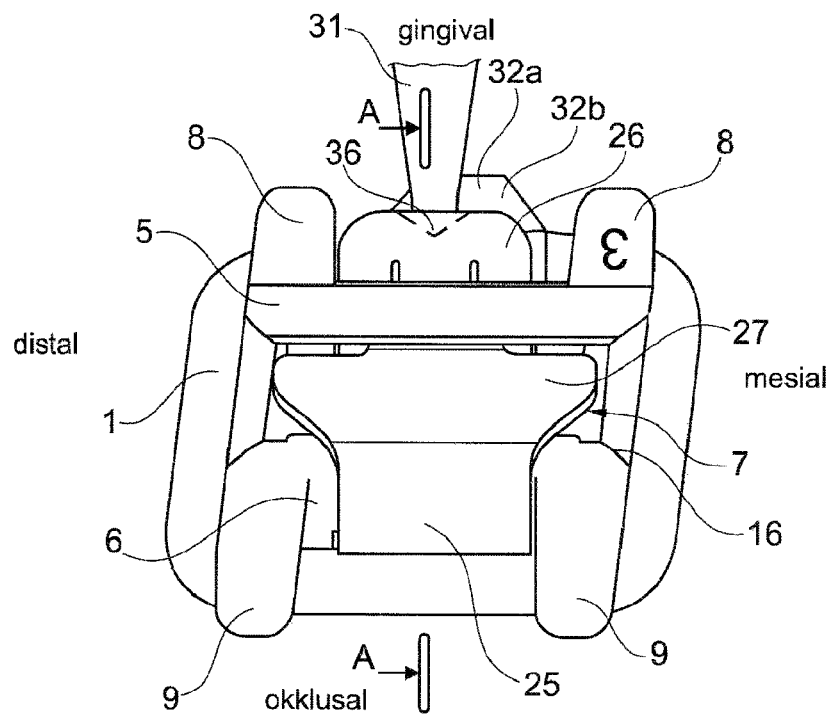
FIG. 1 shows a top view of a bracket with the clip in its closed position.
Figure 2:
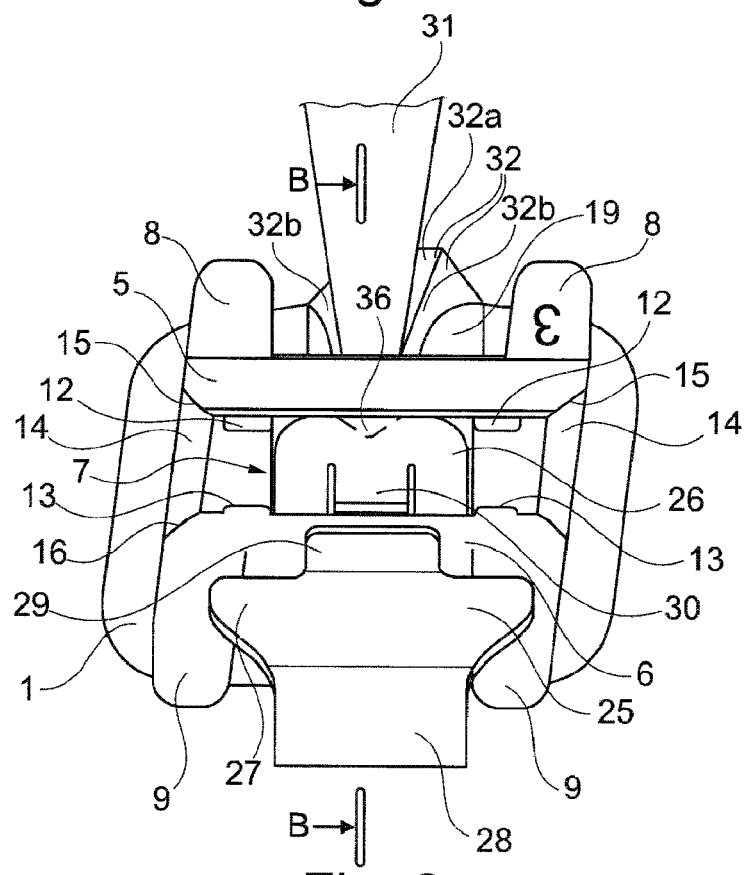
FIG. 2 shows a top view of the bracket with the clip in its open position.

FIG. 1 shows the orientation by way of a tooth on which a bracket is to be mounted with respect to the gingival-to-occlusal and the distal-to-mesial directions.

The base 1 transitions to a support 4 which carries a gingival wall 5 and an occlusal wall 6. The two walls 5 and 6 extend in parallel one to the other and are separated by a slot 7 which extends continuously along a straight line from the distal to the mesial side and which is open in the labial direction.

Two ligature wings 8 projecting in the gingival direction are provided on the gingival wall 5. Two ligature wings 9 projecting in the occlusal direction are provided on the occlusal wall 6. These wings serve for attaching ligature wires in a manner known to the man of the art.

The slot 7 serves to receive an arch wire 10 which, specifically, has a rectangular cross-section. By pre-stressing the arch wire 10, a pressure can be applied on the bottom 11 of the slot 7 and a torque can be applied on the walls 5 and 6 of the bracket. To this end, the clear cross-section of the slot 7 has a substantially rectangular shape. In the present case, it is made slightly narrower by flat ribs 12 of low height on the gingival wall and by flat ribs 13 of low height on the occlusal wall 6, which serve to reduce friction of the arch wire 10 in the slot 7. As will described further below in more detail, the base 11 of the slot 7 does not extend continuously at the same level, but is interrupted. This likewise reduces friction of the arch wire 10 in the slot 7. At the ends of the slot 7, there are provided rounded oblique surfaces 14 on the bottom of the groove, rounded oblique surfaces 15 on the gingival wall 5 and rounded oblique surfaces 16 on the occlusal wall 6 that serve to increase the inlet to the slot 7 and further to reduce the friction encountered by the arch wire 10 in the slot 7; this is especially advantageous in the case of heavy misalignments of the teeth where the arch wire necessarily will have an especially irregular shape.

In the occlusal wall 6, there is provided a channel 17 extending continuously from the distal to the mesial side for receiving some accessory element, such as a spring, a small hook or an accessory wire.

A slot-like passage 18, delimited on its lingual side by a flat surface 19 extending in parallel to the bottom 11 of the slot 7, extends below the bottom 11 of the slot 7 in parallel to the bottom 11 of the slot 7. That surface 19 starts at the occlusal wall 6 and extends crosswise through the bracket, running initially through the support 4 and finally through the gingival portion of the bracket in its base 1. In the vicinity of the ligature wings 8 and 9, the passage 18 is delimited by narrow side walls 20 extending in parallel one to the other and at a right angle to the lingual surface 19. Above the passage 18, the occlusal wall 6 is provided, on its side facing away from the slot 7, with a surface 6a in the form of a cylinder envelope, which transitions in the area of the passage 18 into a flat surface 6b, extending in parallel to the lingual surface 19 and arranged on the labial side of the passage 18. This provides a funnel-like inlet to the passage 18 on the occlusal side of the bracket. Between the side walls 20, the bottom of the slot 7 is lowered to the lingual surface 19 of the passage 18.

In the gingival wall 5, there is provided a window 21 which is bordered by the lingual surface 19, the side walls 20 and oppositely directed projections 22 following the side walls 20, between which an interruption 23 exists in the gingival wall 5, by two edges 34 extending in parallel to the side walls 20 and by a labial edge 35. The lingual edges of the projections 22 are aligned with the labial surface 6b of the passage 18 in the occlusal wall 6 and serve, just as the labial surface 6b, as guides for the lingual leg of the clip 25. The edges 34 and 35, as well as the projections 22, being elements of the window 21, define a substantially rectangular cutout 24, which has a length, measured in the distal-to-mesial direction, greater than the spacing between the projections 22, but smaller than the spacing between the gingival ligature wings 8, and also smaller than the spacing between the ribs 12 and 13, which in the present case is identical to the spacing between the side walls 20. The ribs 12 provided on the gingival wall 5 end at the level of the lingual edge of the rectangular cutout 24, being simultaneously the labial edge of the projections 22.

The bracket comprises a clip 25 made from a spring material. The bracket has a straight lingual leg 26 and, compared with the latter, a shorter labial leg 27 of approximately straight shape. The two legs 26 and 27 are connected by an occlusal section 28 having approximately the shape of an arc of a circle. That section has the same width as the lingual section 26, which fits into the passage 18 with little play. The labial leg 27 widens to approximately the length of the slot 7. It does not extend in parallel, but rather at an acute angle to the lingual leg 26 and approaches the latter on its way from the occlusal section 28. The labial leg 27 is provided on its gingival end with an extension 29, extending in the gingival direction, which is angled in the labial direction. The extension 29 is narrower than the labial leg 27 and narrower than the lingual leg 26; it fits with little play into the cutout 24, which is part of the window 21 in the gingival wall 5.

A tongue 30 is cut out from the lingual leg 26, in the vicinity of its gingival end 26*a*, and is raised at an acute angle relative to the lingual leg 26, in a direction toward the occlusal section 28.

The clip 25 is connected with the bracket by inserting the lingual leg 26, coming from the occlusal direction, into the passage 18. During this process, the tongue 30 is progressively urged through the narrowing inlet of the passage 18 and into the cutout of the lingual leg 26 from which it has been cut out. Once the tongue 30 has passed the occlusal wall 6 it will spring back and will then be directed against the occlusal wall 6 with the result that it can no longer get lost. As the clip 25 is advanced to this position, the extension 29 will hit upon the surface 6*a* of the occlusal wall 6, having the form of a cylinder envelope, and will slide along that wall up to its labial surface, whereby the clip 25 will be expanded against the action of its elastic restoring force. As the clip 25 is further advanced, the labial leg 27 of the clip 25 will slide off the labial surface of the occlusal wall 6 and will spring into the slot 7 where it can come to rest against an arch wire 10. The springing-back action of the clip 25 has the effect to further advance the spring because the spring will be pushed back by the occlusal wall 6 until its extension 29 will engage the cutout 24. One thereby secures the arch wire 10 in the slot 7 as the arch wire 10 cannot lift the labial leg 27 of the clip beyond the point where its extension 29 hits against the labial edge 35 of the cutout 24. The lingual edges 37 of the cutout 24 are simultaneously the labial edges of the projections 22; they determine the smallest spacing between the labial leg 27 of the clip 25 and the bottom 11 of the slot 7. This provides the advantage that thinner arch wires lying in the slot 7, that do not reach the lingual edge 37, will not be exposed to the clamping effect of the clip 25. Such thinner arch wires are often used at the beginning of a treatment for correction of the tooth position and accelerate the correction process provided they are not pinched. Thicker arch wires 10 are in resilient contact with the labial leg 27. In order to reduce friction between the arch wire 10 and the clip 25, the distal and the mesial edges of the labial leg 27 are preferably rounded or provided with an oblique surface.

Figure 3:
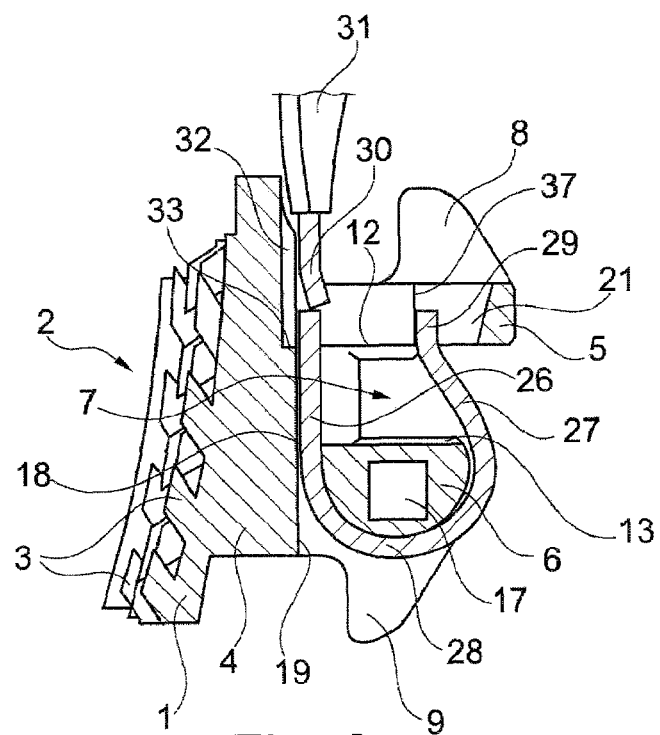
FIG. 3 shows a cross-section of the bracket along line A-A in FIG. 1.
Figure 9:
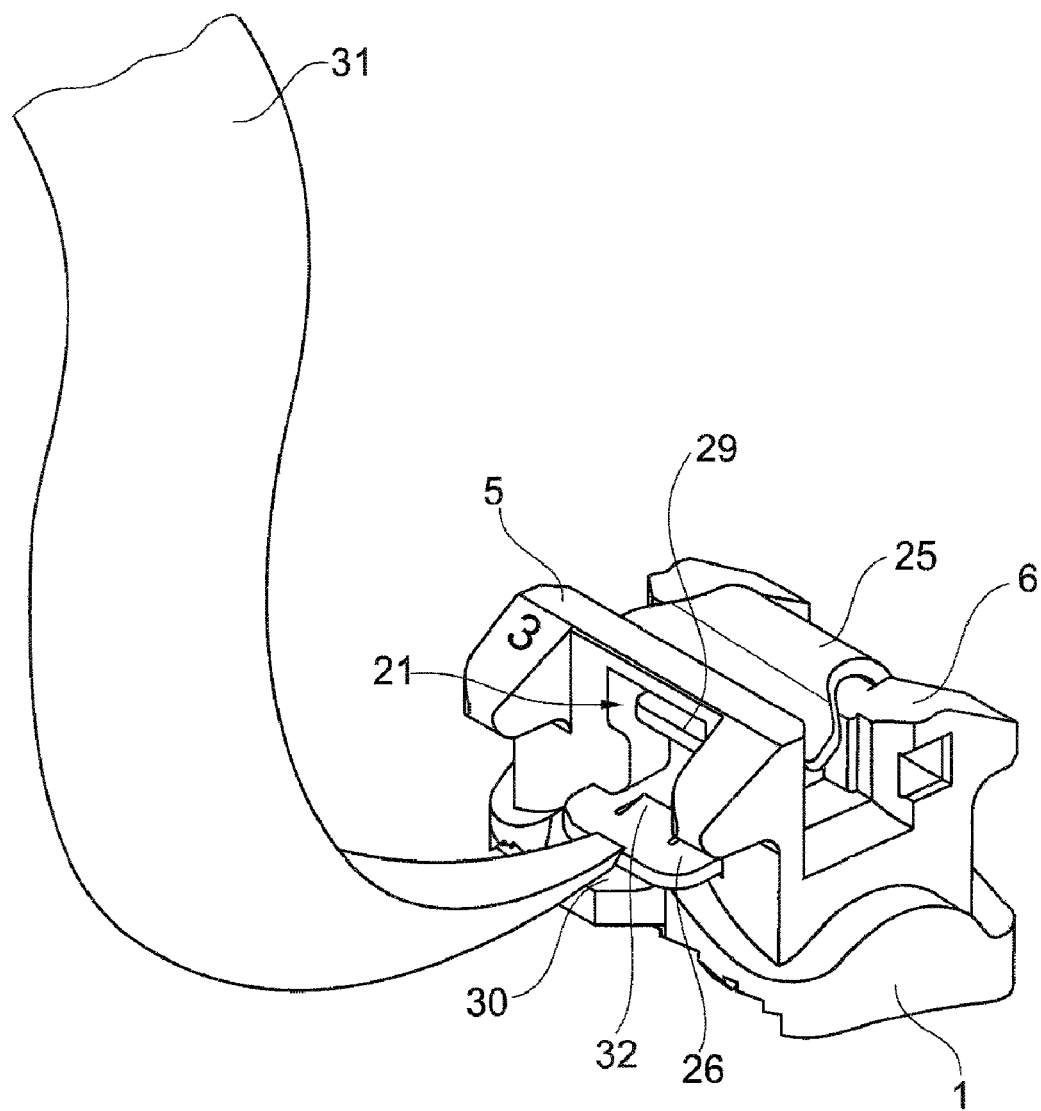
FIG. 9 shows a view of the bracket similar to that of FIG. 5, with a scaler applied.
Figure 10:
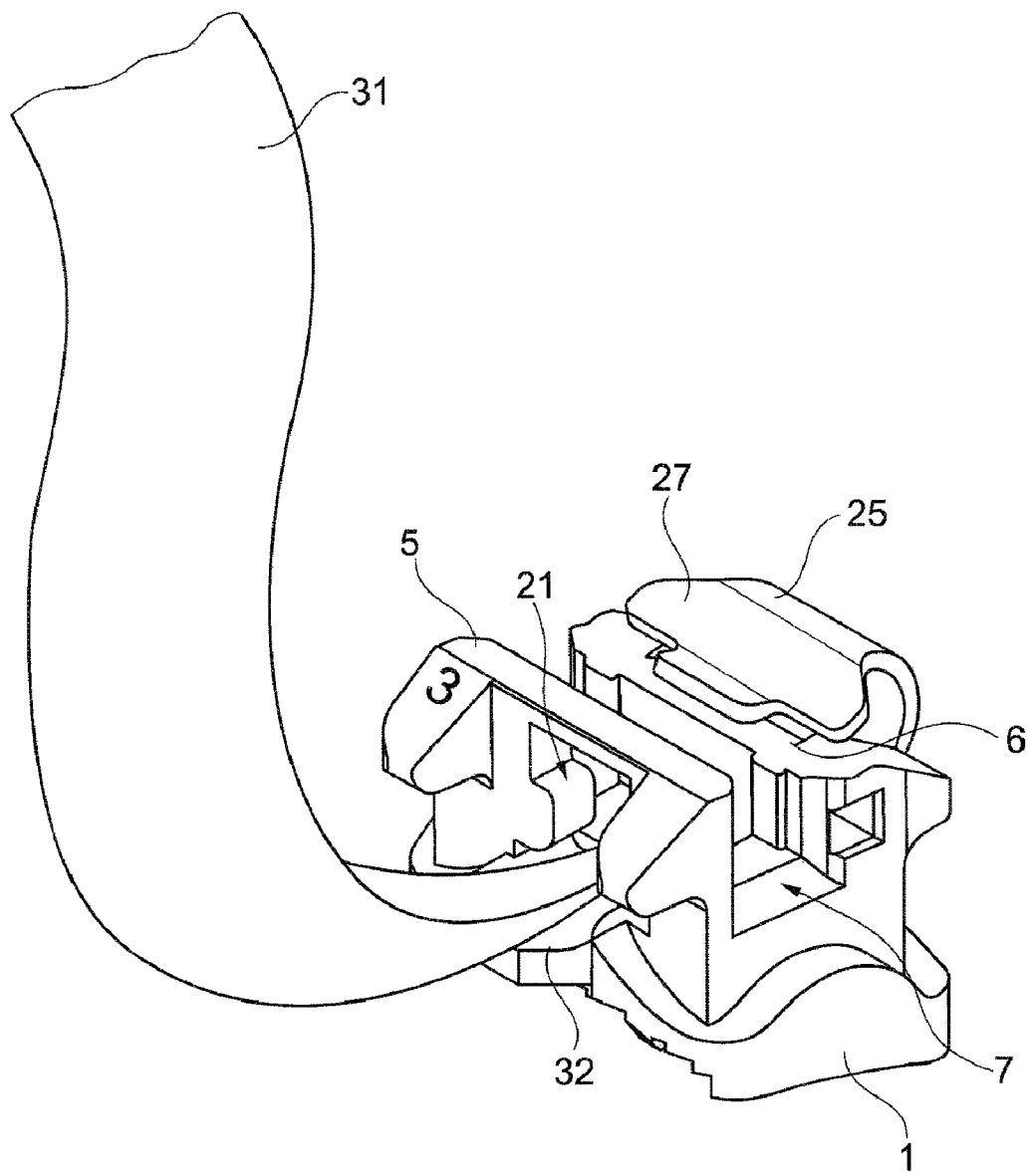
FIG. 10 shows a view of the bracket similar to that of FIG. 6, with a scaler applied.
Figures 11, 12:
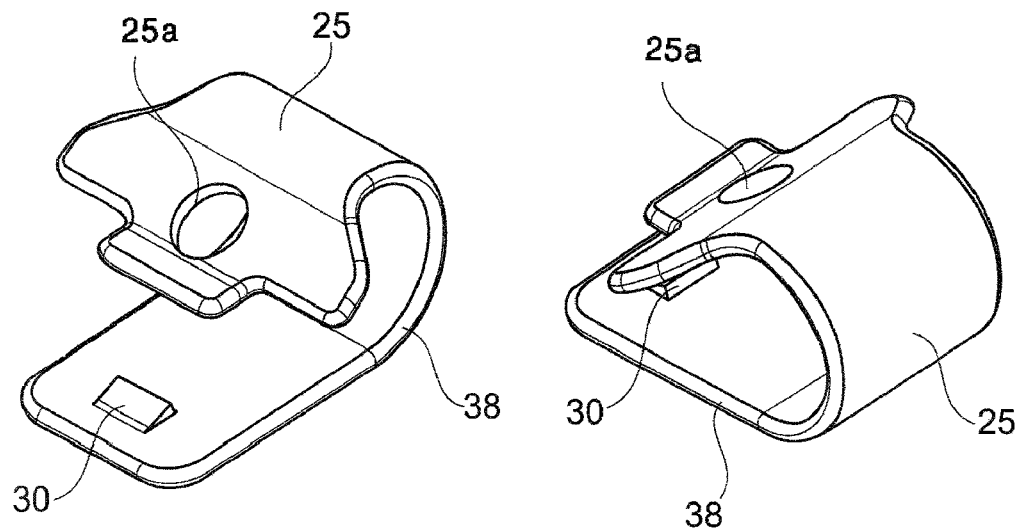
FIG. 11 shows an oblique view of a modified clip for a bracket of the kind illustrated in FIGS. 1 to 10.
FIG. 12 shows an oblique view of the clip of FIG. 11, viewed from a different angle.
Figures 13, 14:
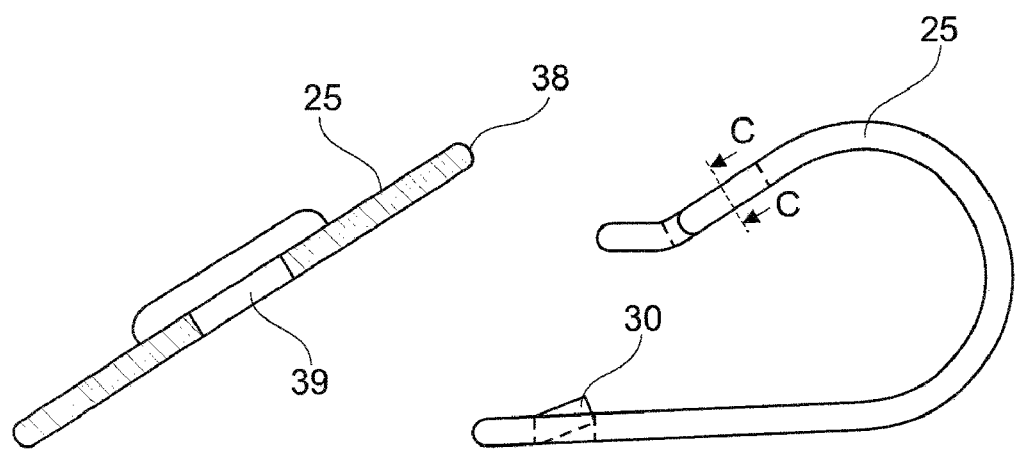
FIG. 13 shows a side view of a clip according to FIG. 11.
FIG. 14 shows a cross-section through the clip according to FIG. 13, taken along line C-C.

For transferring the clip 25 from its closed position (FIG. 1, FIG. 3, FIG. 5, FIG. 9) to its open position (FIG. 2, FIG. 4, FIG. 6, FIG. 10), one takes a tool 31, for example a scaler, and applies it to the gingival edge of the lingual leg 26, as illustrated in FIGS. 1, 3 and 9. One can feel this point, without having to see it, because a surface 19, which delimits the passage 18 on its lingual side, extends in the gingival direction so far that it comes to project beyond the gingival end of the lingual leg 26 of the clip 25. Further, a groove 32 provided in the lingual surface 19 starts out from the gingival end of that surface and extends to a point below the lingual leg 26. That groove 32 has an approximately flat central portion 32*a*, flanked by two concave sections 32*b*, which provide a transition between the central section 32*a* and the lingual surface 19. The groove 32 narrows in the gingival-to-occlusal direction and ends at a stop 33. The groove 32 serves as positioning aid for the tool 31, which serves to feel the groove 32. Once the groove 32 has been found, the clip 25 is displaced in the gingival-to-occlusal direction using the tip of the tool 31, the tip of the tool 31 being further guided in the correct direction by the groove 32. The displacing movement ends when the tool 31 hits against the stop 33. The stop 33 is located so that the tongue 30 will occupy a position a short way before the occlusal wall 6, indicated in FIG. 4, when the tool 31 hits upon the stop 33 during displacement of the clip 25. The clip 25 then is in its open position. In this open position, the labial leg 27 of the clip is in its rest position on the occlusal wall 6, in which it frees the access to the slot 7 from the labial direction.

Figure 4:
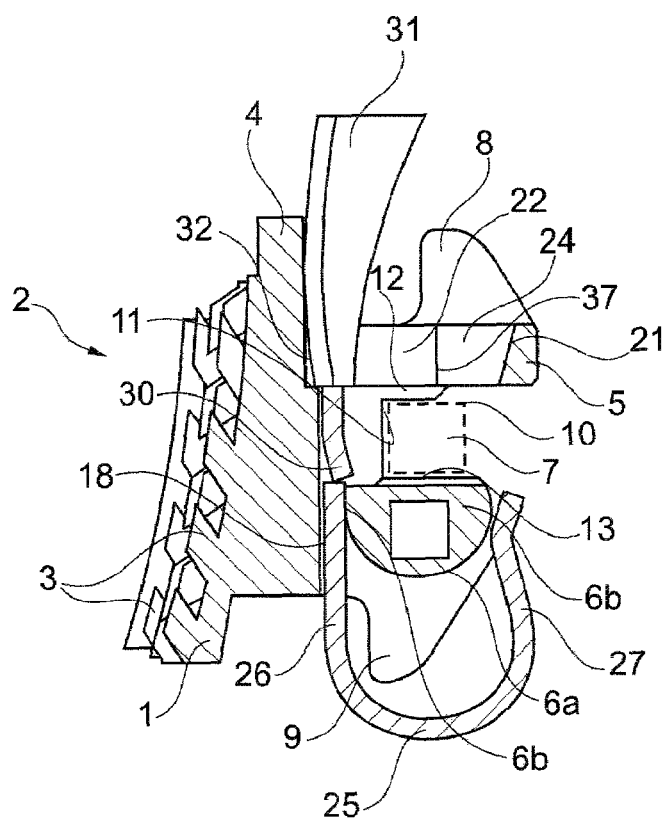
FIG. 4 shows a cross-section of the bracket along line B-B in FIG. 2.
Figure 5:
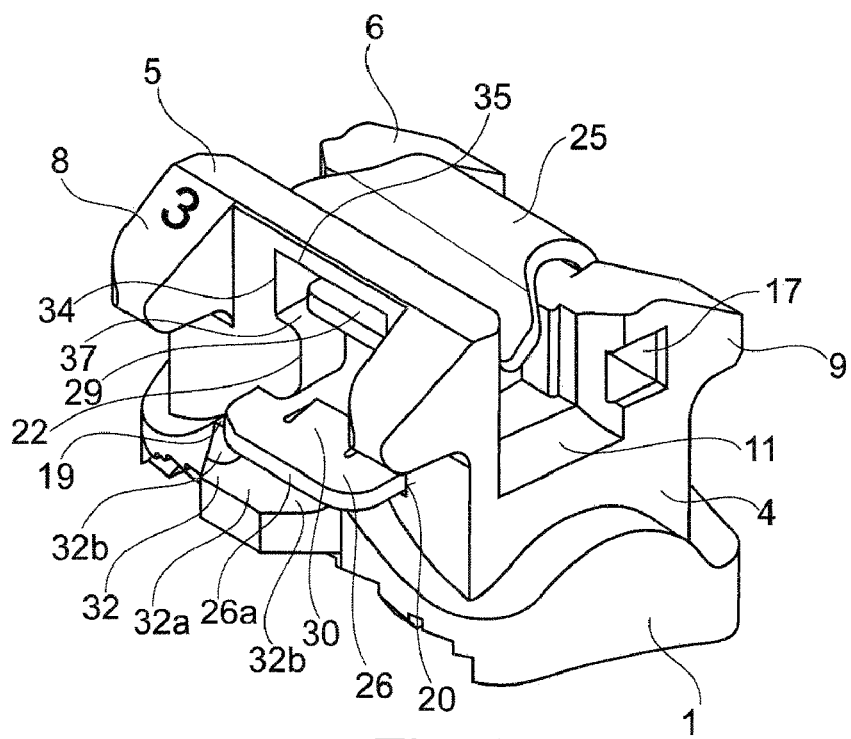
FIG. 5 shows an oblique view of the gingival and labial side of the bracket according to FIGS. 1 and 3.
Figure 6:
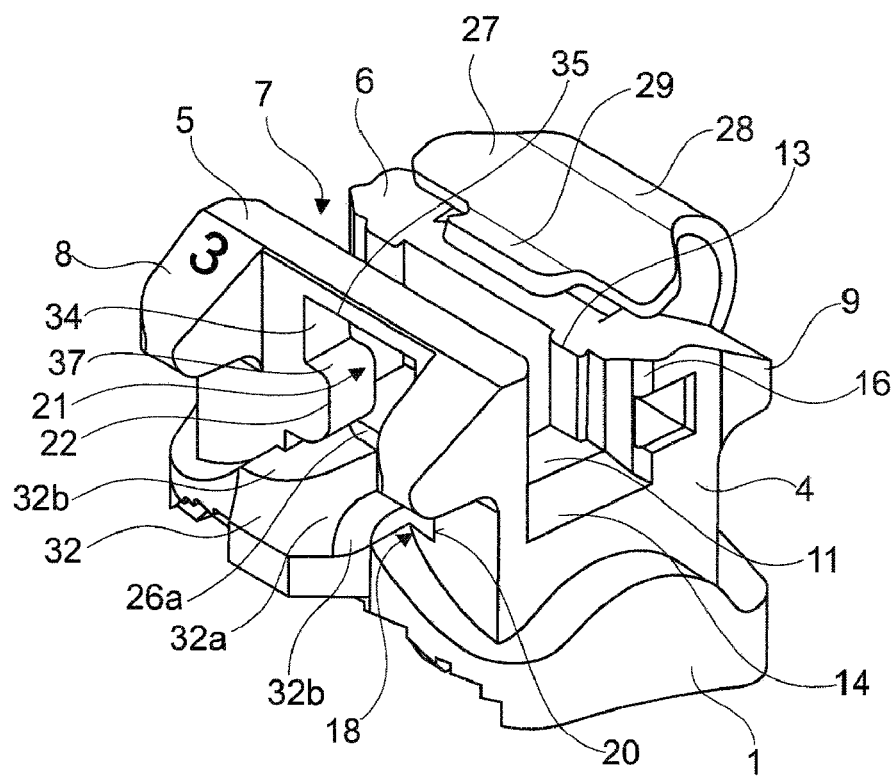
FIG. 6 shows an oblique view of the gingival and labial side of the bracket according to FIGS. 2 and 4.
Figure 7:
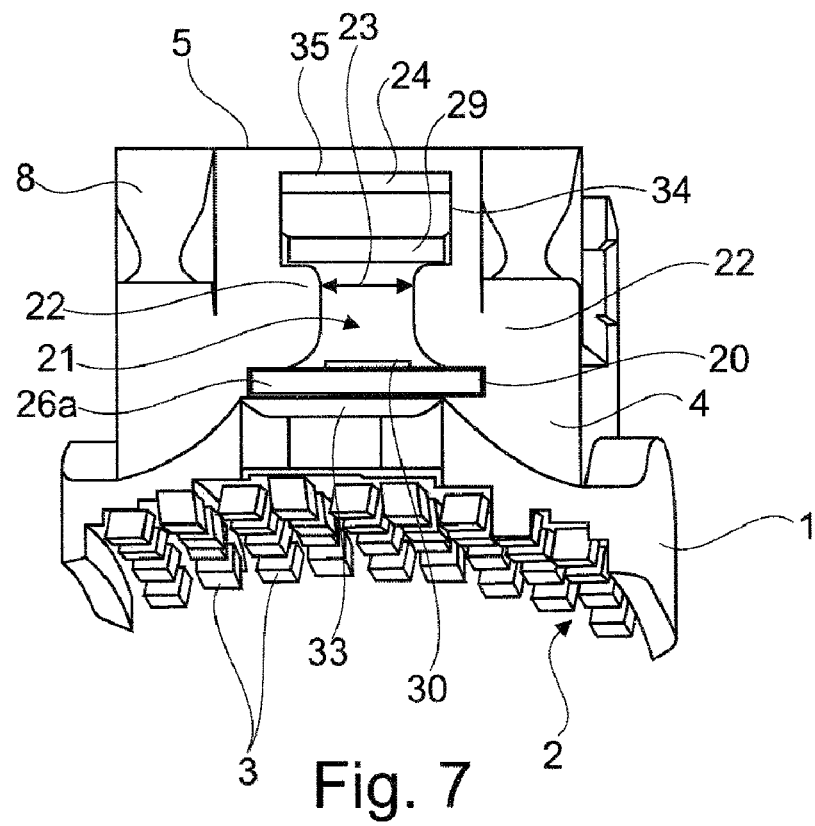
FIG. 7 shows an oblique view of the gingival and labial side of the bracket according to FIG. 5.
Figure 8:
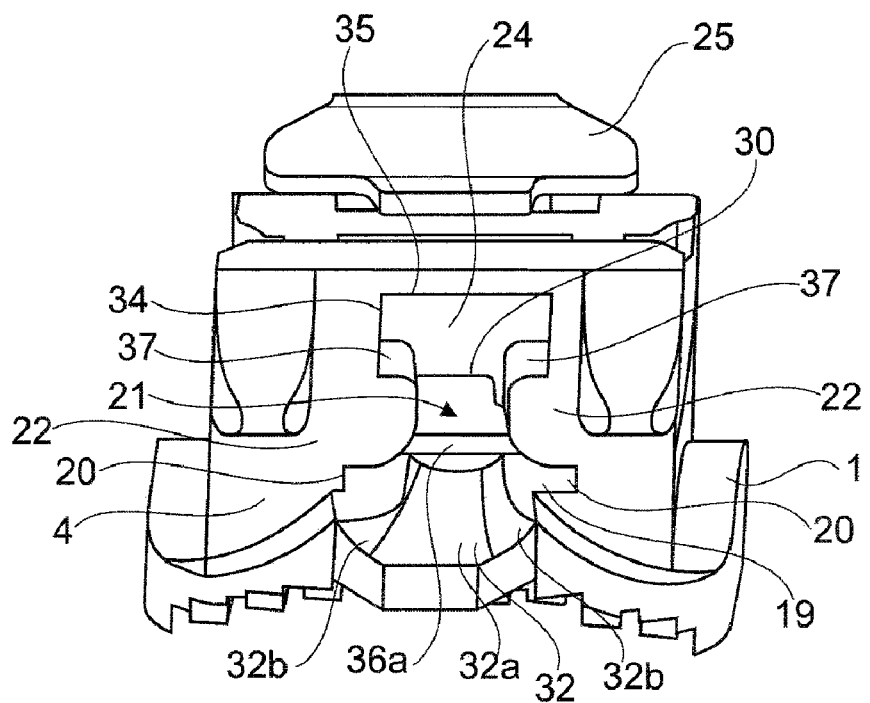
FIG. 8 shows an oblique view of the gingival and labial side of the bracket, viewed from the gingival side, with the bracket in its open position.

Even if the stop 33 should be overcome by the tool 31, the clip 25 can be displaced in the occlusal direction only until the tongue 30 hits against the occlusal wall 6. Thus, the clip 25 cannot get lost during transfer from its closed position (FIG. 3) to its open position (FIG. 4). For completely separating the clip 25 from the bracket, it is necessary to urge the tongue 30 back into the recess from which is has been cut out using a tool, and to push or pull the clip 25 a further distance in the occlusal direction with the tongue 30 in pressed-down condition.

A notch 36, indicated in the drawings by broken lines only, may be provided centrally on the gingival edge of the lingual leg 26 of the clip 25. That notch may serve as a positioning aid instead of the groove 32 or in addition to the groove 32.

FIGS. 11 to 14 show a modified clip 25 which differs from the clip 25 illustrated in FIGS. 1 to 10 in that its entire edge 38 is rounded. Such rounded configuration is of special advantage in the region of the slot 7 because it allows low-friction movement of the arch wire 10. A hole 25*a* in the clip 25 allows a tool to be engaged for displacement of the clip 25 on the bracket.

Figure 15:
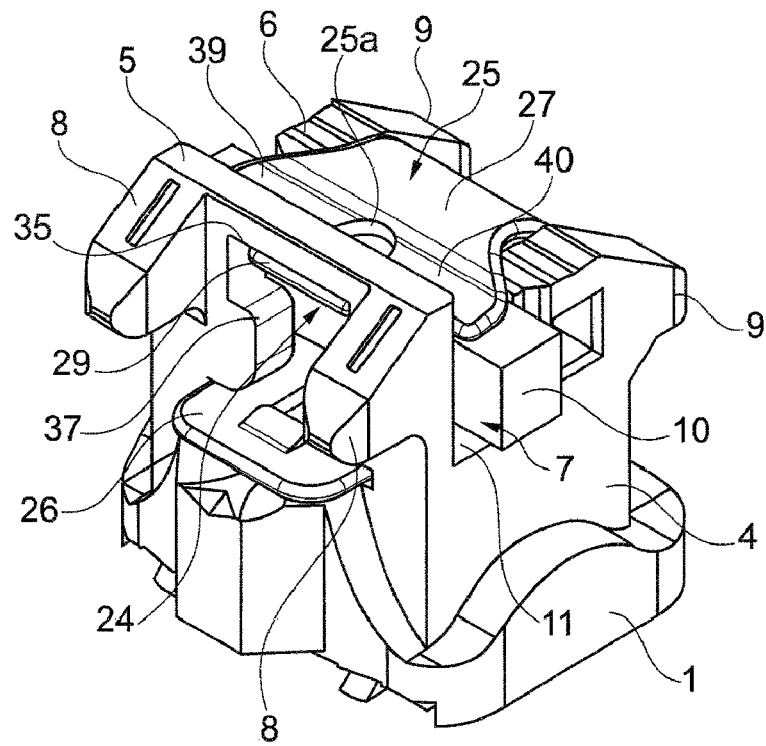
FIG. 15 shows an oblique view of a bracket corresponding to FIG. 5, but with a modified clip.
Figure 16:
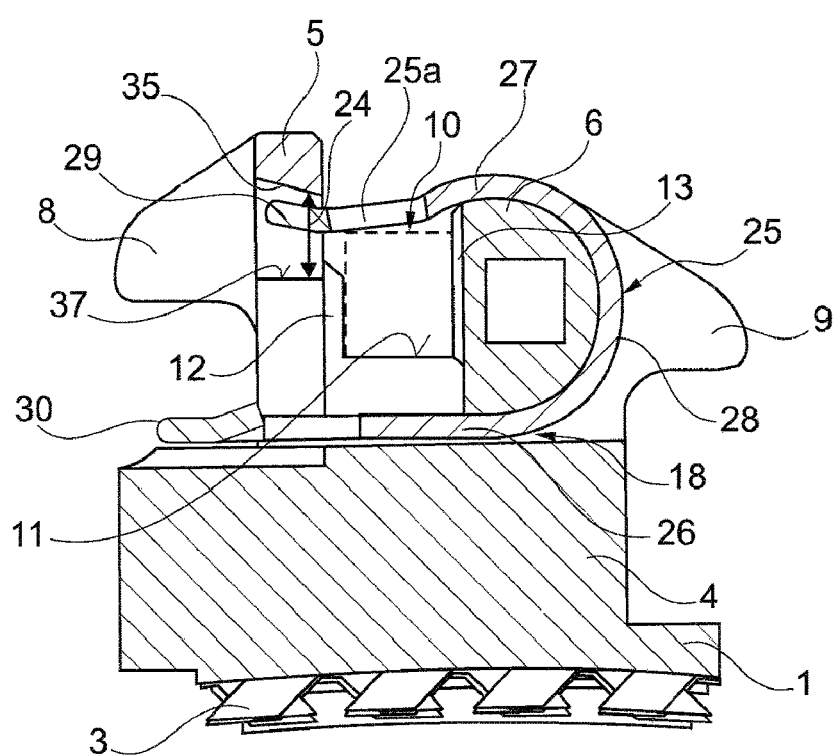
FIG. 16 shows a cross-section similar to that of FIG. 3 through the bracket illustrated in FIG. 15.

The bracket illustrated in FIGS. 15 and 16 differs from that illustrated in FIGS. 1 to 10 essentially by the use of a modified clip 25. The essential difference is not seen in the hole 25*a* in the labial leg 27, provided in the case of the clip 25 illustrated in FIGS. 11 to 14. Rather, the clip 25 of the example illustrated in FIGS. 15 and 16 is bent to a lesser degree than in FIGS. 1 to 10. This has the result that the extension 29 of the labial leg no longer comes to lie on the lingual edge 37 of the projections 22 that delimit the cutout 24 on the lingual side and that form a lingual stop for the labial leg 27 of the clip 25 in FIGS. 1 to 10, without any action of an arch wire 10. Instead, the extension 29 of the labial leg 27 comes to lie closely below the labial edge 35 of the cutout 24 that forms a labial stop for the extension 29 of the labial leg 27 of the clip 25. The extension 29 may be in contact with the stop 25, but the clip 25 can be moved to its closed position, as illustrated in FIG. 16, more easily when a small spacing is left between the extension 29 and the stop 35; that small spacing should be small compared with the spacing of the labial stop 35 from the lingual stop 37.

The two wings 39 and 40 provided on the labial leg 27 are located on the labial leg 27 in the neighborhood of the extension 29 and extend in distal and/or in mesial direction. In the closed position of the clip 25, they are positioned above the slot or in the upper region of the slot 7, which is delimited by them in the labial direction.

The edge of the wings 39 and 40 is rounded. The edge of the wings on the gingival side of the wings 39 and 40 is straight and extends substantially in parallel to the gingival wall 5. The occlusal edge of the wings 39 and 40 in contrast extends at an acute angle relative to the gingival wall 5 so that the wings 39 and 40 taper toward their tips, thereby favoring low-friction adaptation of the wings to an arch wire 10.

Figure 17:
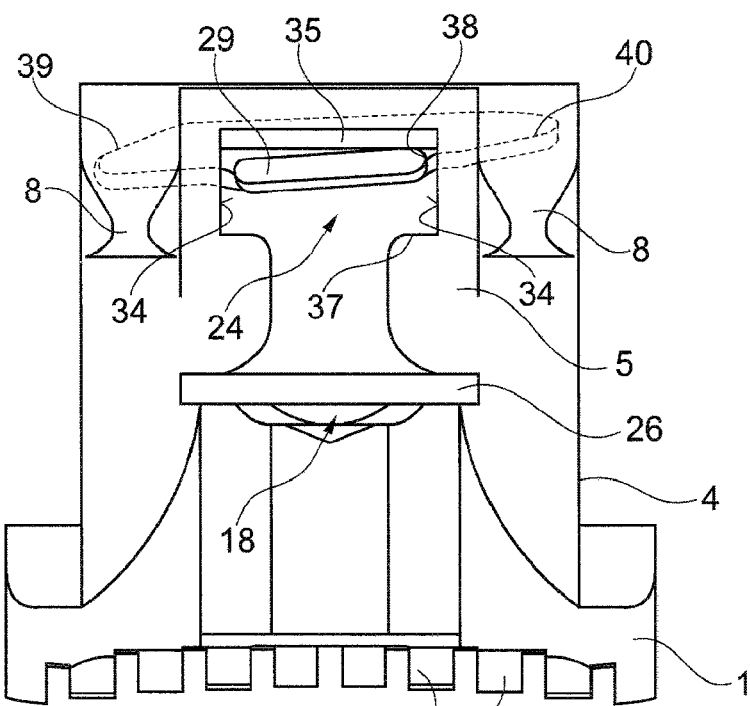
FIG. 17 shows a view of the gingival side of the bracket illustrated in FIG. 15.

FIG. 17 shows the typical position, viewed from the gingival side, of the labial leg 27 of the clip 25 in a bracket similar to the one shown in FIGS. 15 and 16, which would be obtained under load by an arch wire 10 which extends obliquely through the slot 7, from the lingual to the labial direction, and which loads the wing 40 more heavily than the wing 39. The extension 29 is in this case allowed to tilt about its rounded edge 38, neighboring the wing 40, into the oblique position illustrated in FIG. 17, thereby building up a torsional strain in the labial leg 27. The labial edge 35 of the cutout 24, against which the extension 29 abuts, is in this case rectilinear and extends in parallel to the bottom 11 of the slot 7.

Figure 18:
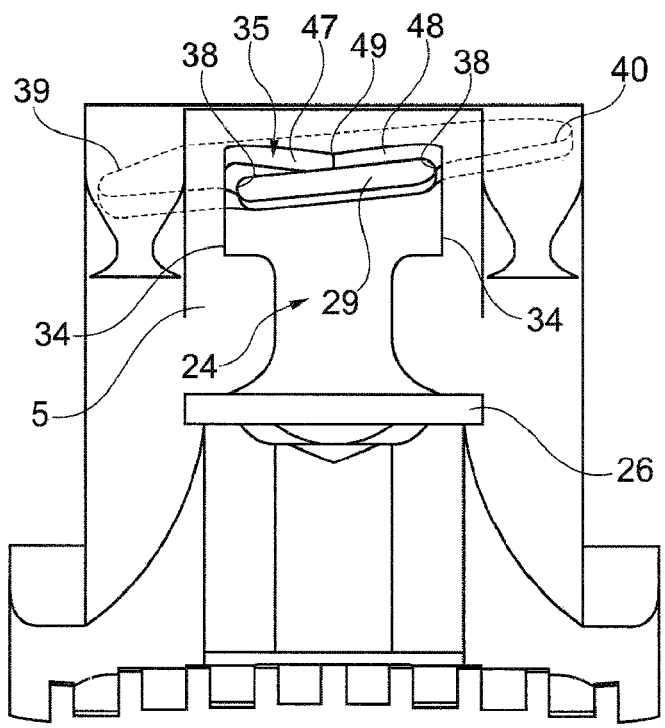
FIGS. 18 to 20 show a view, similar to FIG. 17, of modified brackets.

Tilting of the extension 29 of the labial leg 27 is facilitated when the contour of the labial edge 35 is modified relative to that shown in FIG. 17 in the way illustrated in FIG. 18. In this case, the labial edge 35 projects in lingual direction, thereby forming a central angle point 49 from which two straight sections 47 and 48 lead to the distal and mesial edges 34 of the cutout 24. The two straight sections 47 and 48 extend at an angle one relative to the other that is slightly larger than 180°. The labial edge 35 is set back relative to the angle point 49 toward the mesial and distal edges 34, whereby room is provided for the extension 29 that is tilted into that space until it abuts against the straight section 48. Any further tilting movement is obstructed by a sudden rise in resistance which can be overcome only by building up an additional torsional strain that has the result to elastically bend the wing 40 as well.

Figure 19:
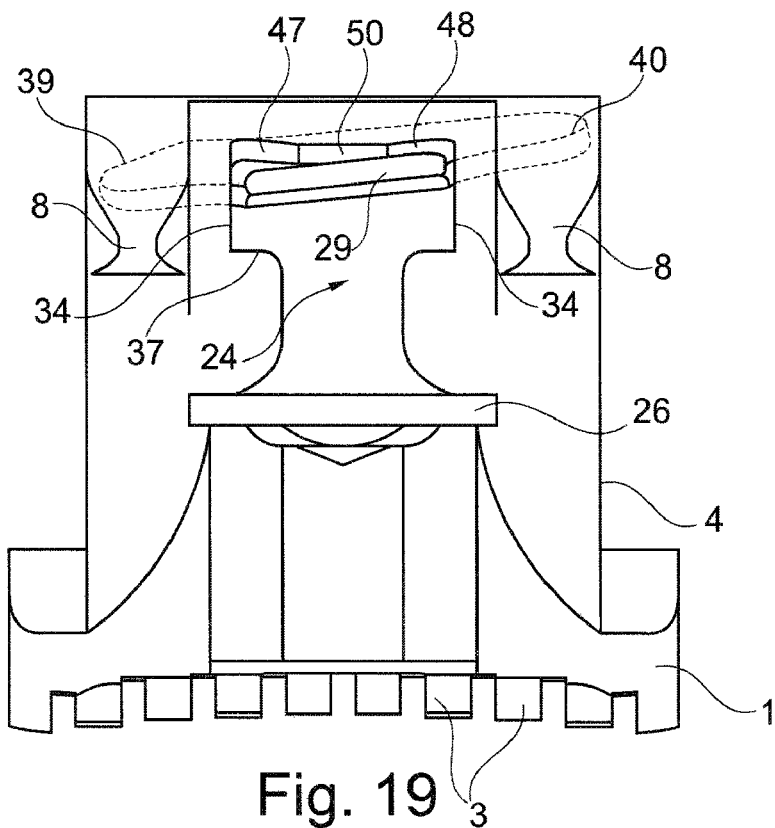

The embodiment illustrated in FIG. 19 differs from that illustrated in FIG. 18 in that a third, centrally arranged straight section 50, extending in parallel to the bottom of the slot 7, is provided between the two straight sections 47 and 48 of the labial edge 35. The section 50 forms a flat stop on which the extension 29 comes to rest in a stable position when the two wings 39 and 40 are loaded approximately symmetrically by an arch wire 10. The wings 39 and 40 can be bent in that position by the arch wire 10 in radial direction.

Figure 20:
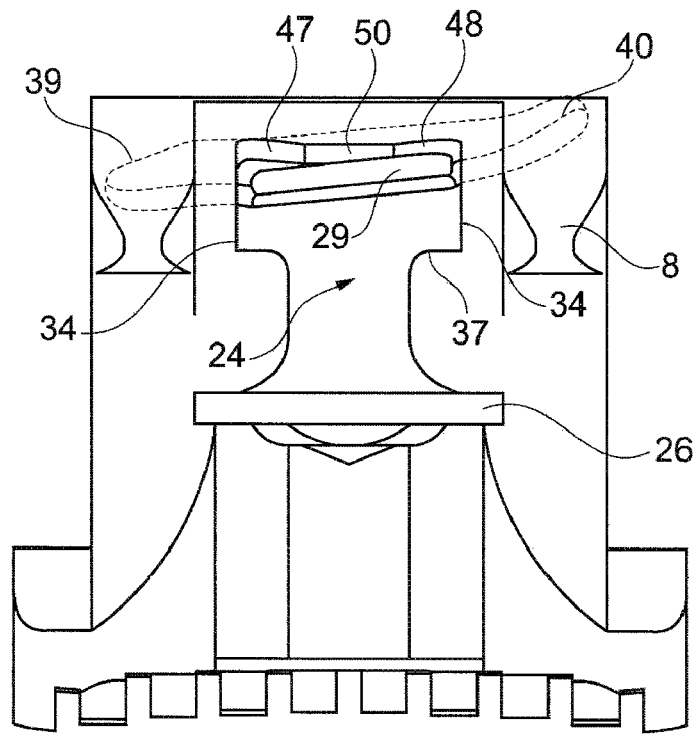

FIG. 20 shows the bracket illustrated in FIG. 19, but with the wing 40 exposed to higher unilateral loading with the dual effect that the extension 29 tilts toward the straight section 48, as shown in FIG. 19, and that additionally the wing 40 is clearly bent in labial direction.

Figure 21:
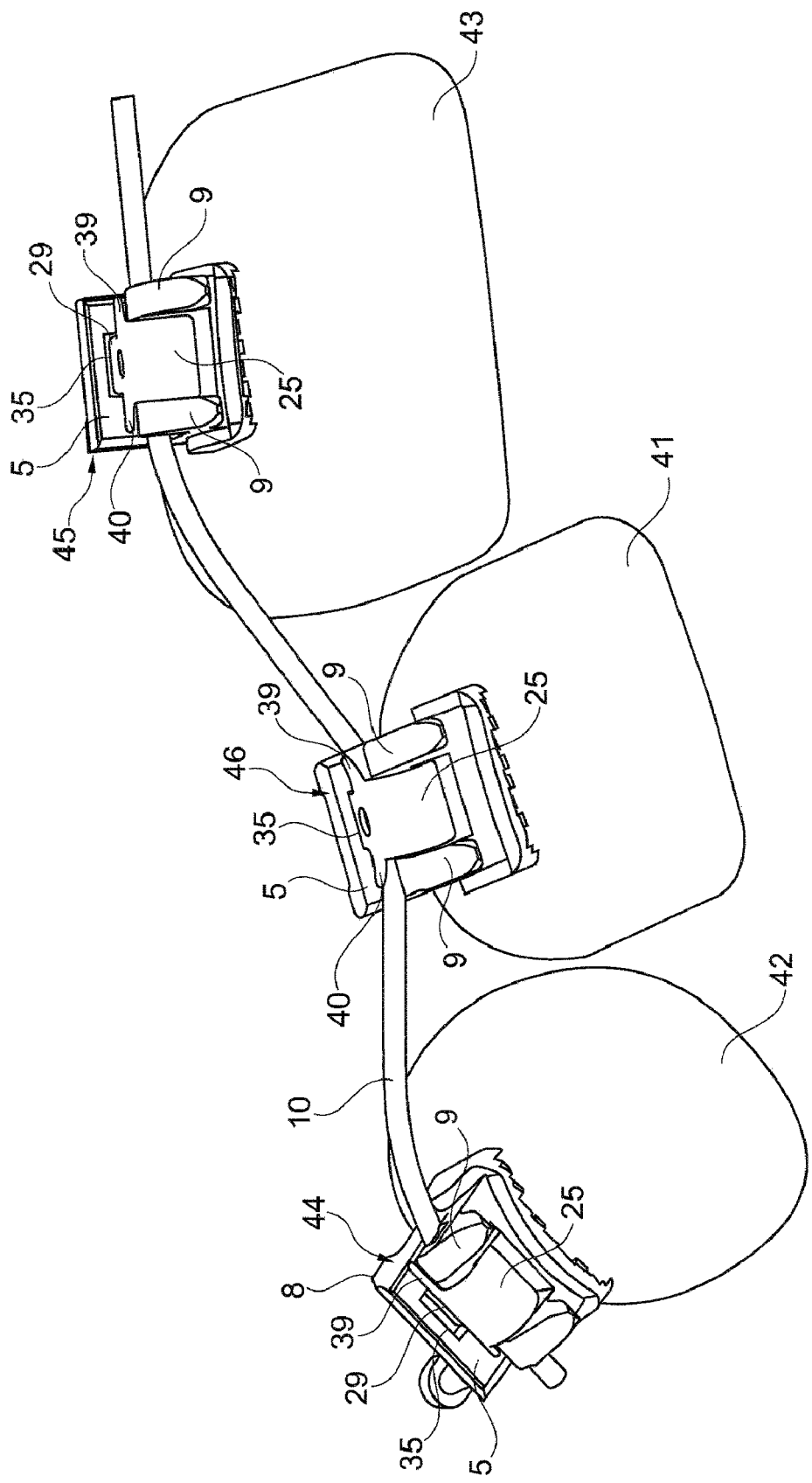
FIGS. 21 and 22 show two exemplary applications of the invention.

FIG. 21 shows one example of an embodiment for the correction of the position of a tooth 41, where the tooth exhibits an initial position, shifted to the lingual direction, from which is to be moved into a gap that exists between two teeth 42 and 43 in normal position. To this end, brackets 44, 45, 46, respectively, of the same basic structure are bonded to each of the three teeth 41, 42, 43. The brackets 44 and 45 comprise a clip 25 of the type illustrated in FIGS. 11 to 14 (described as the "second" clip in Claim 5) and in an arrangement of the kind illustrated in FIGS. 1 to 10, which means that the extension 29 of the labial leg 27 urges the arch wire 10 against the bottom of the slot 7. Contrary to that arrangement, the tooth 41 to be displaced is provided with a bracket 46 with a clip 25' (described as the "first" clip in Claim 5) of the configuration illustrated in FIGS. 15 and 16, which means that the extension 29 of the labial leg of the clip 25' is in contact, or nearly in contact, with the stop 35, even without being loaded by the arch wire 10. The tensioned arch wire 10, fitted in the three brackets 44, 45 and 46, resiliently deflects both wings 39 and 40 of the clip 25' in the bracket 46 so that they adapt themselves to the arch wire 10 along a curve. While they increase the corrective force that acts on the tooth 41, the friction exerted by them on the tooth 41 is low enough to substantially accelerate the process of correction of the position of the tooth 41.

Figure 22:
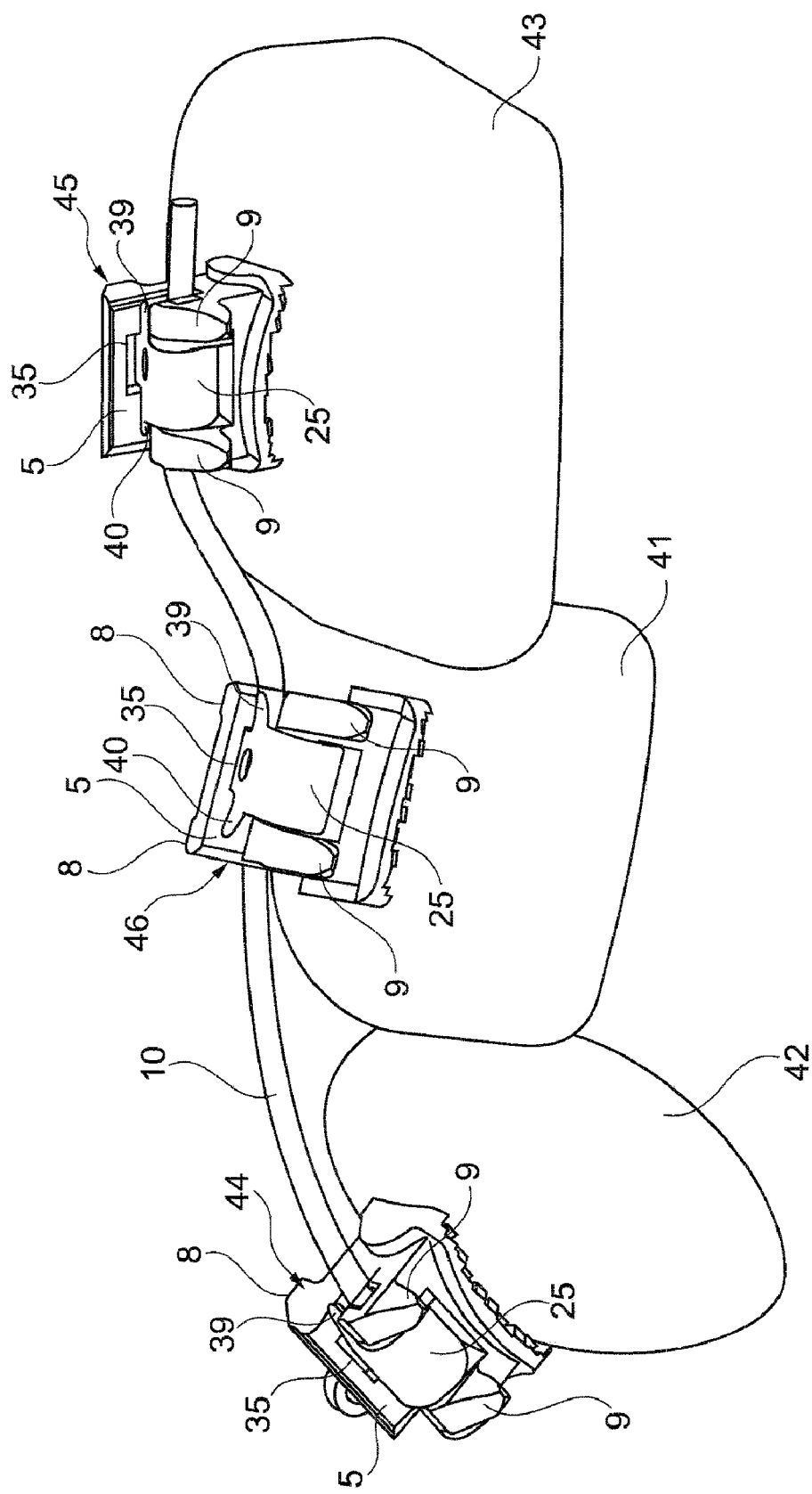

The embodiment illustrated in FIG. 22 differs from that illustrated in FIG. 21 in that the tooth 41 to be corrected is to be brought into its target position by rotation. The arch wire 10 therefore resiliently deflects only the wing 39 of the clip 25' in the bracket 46. The wing 40 is not in contact with the arch wire 10. Correction of the tooth position is accelerated in this case as well.

LIST OF REFERENCE NUMERALS

1. Base
2. Bottom surface of 1
3. Projections
4. Support
5. Gingival wall
6. Occlusal wall
6a. Surface having the form of a cylinder envelope
6b. Labial surface
7. Slot
8. Gingival ligature wing
9. Occlusal ligature wing
10. Arch wire
11. Bottom of 7
12. Ribs on 5
13. Ribs on 6
14. Oblique surfaces on 11
15. Oblique surfaces on 5
16. Oblique surfaces on 6
17. Channel
18. Passage
19. Lingual surface
20. Side walls
21. Window in 5
22. Projections in 5
23. Interruptions in 5
24. Cutout
25. Clip
25'. Clip
25a. Hole
26. Lingual leg
26a. Gingival end
27. Labial leg
28. Occlusal section of 25
29. Extension of 27
30. Tongue
31. Tool
32. Groove
32a. Central section of 32
32b. Lateral sections of 32
33. Stop
34. Edges of 21
35. Labial edge of 21, labial stop
36. Notch
37. Lingual edges of 21, lingual stop
38. Edge of 25
39. Wing
40. Wing 41. Tooth
42. Tooth
43. Tooth
44. Bracket
45. Bracket
46. Bracket
47. Straight section of 35
48. Straight section of 35
49. Angle point
50. Straight section of 35

The invention claimed is:

1. Self-ligating bracket for use in orthodontics having the following features:

The bracket comprises a base;
a support arranged on the base;
an occlusal wall with at least one occlusal ligature wing extending from the support;
a gingival wall with at least one gingival ligature wing extending from the support;
a slot separating the occlusal wall from the gingival wall and extending continuously in the mesial-to-distal direction;
a passage which extends continuously through the support in the gingival-to-occlusal direction; and
a resilient clip having a labial leg and a lingual leg that are connected one to the other by a section on the occlusal or the gingival side;
the lingual leg is received in the passage and is arranged for displacement in the passage only in the gingival-to-occlusal direction, between a closed position and an open position of the clip;
in the closed position, the labial leg extends into a cutout in the gingival wall or in the occlusal wall, respectively, which is provided with a stop for the labial leg, at least in the labial direction;
in the open position, the tip of the labial leg is positioned above the occlusal wall or above the gingival wall, respectively;
the labial leg of the clip is provided with a wing extending in distal direction and a wing extending in mesial direction;
in the closed position of the clip the wings are positioned above the slot or in the labial region of the slot, whereas a lingual extension of the labial leg of the clip is positioned in the cutout, the extension being narrower than the width of the labial leg, measured across the wings;
the extension of the labial leg of the clip is in contact, or nearly in contact with the labial stop, in the closed position of the clip, even when the slot is empty, a labial edge of the cutout has two straight sections that extend at an angle of more than 180° one relative to the other.

2. The bracket as defined in claim 1, wherein the wings do not extend into the cutout.

3. The bracket as defined in claim 1, wherein the edge of the wings is rounded.

4. The bracket as defined in claim 1, wherein the width of the wings decreases toward their tips.

5. The bracket as defined in claim 1, wherein the wings are curved in labial direction.

6. The bracket as defined in claim 1, wherein the wings oppose a lesser resistance to bending in labial direction than the main portion of the clip from which the wings project.

7. The bracket as defined in claim 6, wherein the wings are thinner or softer than the main portion of the clip.

8. The bracket as defined in claim 6, wherein the material of the clip is weakened between the wings and the main portion of the clip.

9. The bracket as defined in claim 1, wherein the width of the extension of the labial leg of the clip and the dimensions of the cutout in the gingival wall or in the occlusal wall, respectively, are adapted one to the other so that the labial leg will not be plastically deformed by an arch wire due to torsional strain in the course of an orthodontic treatment.

10. Self-ligating bracket for use in orthodontics having the following features:

The bracket comprises a base;
a support arranged on the base;
an occlusal wall with at least one occlusal ligature wing extending from the support;
a gingival wall with at least one gingival ligature wing extending from the support;
a slot separating the occlusal wall from the gingival wall and extending continuously in the mesial-to-distal direction;
a passage which extends continuously through the support in the gingival-to-occlusal direction; and
a resilient clip having a labial leg and a lingual leg that are connected one to the other by a section on the occlusal or the gingival side;
the lingual leg is received in the passage and is arranged for displacement in the passage only in the gingival-to-occlusal direction, between a closed position and an open position of the clip;
in the closed position, the labial leg extends into a cutout in the gingival wall or in the occlusal wall, respectively, which is provided with a stop for the labial leg, at least in the labial direction;
in the open position, the tip of the labial leg is positioned above the occlusal wall or above the gingival wall, respectively;
the labial leg of the clip is provided with a wing extending in distal direction and a wing extending in mesial direction;
in the closed position of the clip the wings are positioned above the slot or in the labial region of the slot, whereas a lingual extension of the labial leg of the clip is positioned in the cutout, the extension being narrower than the width of the labial leg, measured across the wings;
the labial stop is formed on a labial edge of the cutout that projects in lingual direction in the region between a distal and a mesial edge, the labial edge of the cutout has two straight sections that extend at an angle of more than 180° one relative to the other.

11. The bracket as defined in claim 10, wherein the extension of the labial leg of the clip is in contact, or nearly in contact with the labial stop, in the closed position of the clip, even when the slot is empty.

12. Self-ligating bracket for use in orthodontics having the following features:

The bracket comprises a base;
a support arranged on the base;
an occlusal wall with at least one occlusal ligature wing extending from the support;
a gingival wall with at least one gingival ligature wing extending from the support;
a slot separating the occlusal wall from the gingival wall and extending continuously in the mesial-to-distal direction;
a passage which extends continuously through the support in the gingival-to-occlusal direction; and
a resilient clip having a labial leg and a lingual leg that are connected one to the other by a section on the occlusal or the gingival side;

the lingual leg is received in the passage and is arranged for displacement in the passage only in the gingival-to-occlusal direction, between a closed position and an open position of the clip;

in the closed position, the labial leg extends into a cutout in the gingival wall or in the occlusal wall, respectively, which is provided with a stop for the labial leg, at least in the labial direction;

in the open position, the tip of the labial leg is positioned above the occlusal wall or above the gingival wall, respectively;

the labial leg of the clip is provided with a wing extending in distal direction and a wing extending in mesial direction, in the closed position of the clip the wings are positioned above the slot or in the labial region of the slot, whereas a lingual extension of the labial leg of the clip is positioned in the cutout, the extension being narrower than the width of the labial leg, measured across the wings;

the labial stop is formed on a labial edge of the cutout that projects in lingual direction in the region between a distal and a mesial edge, wherein the labial edge of the cutout has two straight sections that extend at an angle of more than 180° one relative to the other.

13. The bracket as defined in claim 12, wherein the labial edge of the cutout projects in lingual direction mirror-symmetrically relative to its center plane that crosses the slot.

14. The bracket as defined in claim 12, wherein the central portion of the labial edge of the cutout projects the farthest in lingual direction.

15. The bracket as defined in claim 12, wherein the labial edge of the cutout has a convex shape.

16. The bracket as defined in claim 12, wherein the two straight sections of the labial edge of the cutout extend from a common angle point.

17. The bracket as defined in claim 12, wherein the two sections of the labial edge of the cutout that extend at an angle of more than 180° one relative to the other are connected by a third straight section.

18. The bracket as defined in claim 17, wherein the third straight section of the labial edge of the cutout extends in parallel to the bottom of the slot.

19. A method for using an orthodontic bracket having
a base;
a support arranged on the base;
an occlusal wall with at least one occlusal ligature wing extending from the support;
a gingival wall with at least one gingival ligature wing extending from the support;
a slot separating the occlusal wall from the gingival wall and extending continuously in the mesial-to-distal direction;
a passage which extends continuously through the support in the gingival-to-occlusal direction; and
a resilient clip having a labial leg and a lingual leg that are connected one to the other by a section on the occlusal or the gingival side;
the lingual leg is received in the passage and is arranged for displacement in the passage only in the gingival-to-occlusal direction, between a closed position and an open position of the clip;
in the closed position, the labial leg extends into a cutout in the gingival wall or in the occlusal wall, respectively, which is provided with a stop for the labial leg, at least in the labial direction;
in the open position, the tip of the labial leg is positioned above the occlusal wall or above the gingival wall, respectively;
the labial leg of the clip is provided with a wing extending in distal direction and a wing extending in mesial direction;
in the closed position of the clip the wings are positioned above the slot or in the labial region of the slot, whereas a lingual extension of the labial leg of the clip is positioned in the cutout, the extension being narrower than the width of the labial leg, measured across the wings;
the extension of the labial leg of the clip is in contact, or nearly in contact with the labial stop, in the closed position of the clip, even when the slot is empty, a labial edge of the cutout has two straight sections that extend at an angle of more than 180° one relative to the other comprising the steps of correcting the position of teeth which are misaligned, an arch wire lying in the slot resiliently deflecting at least one wing in a labial direction during the corrective treatment.

20. The method according to claim 19, comprising the steps of rotating a tooth or displacing a tooth in the lingual-to-labial direction or in the labial-to-lingual direction.

21. The method according to claim 19, wherein the width of the labial leg, measured across the wings, is not greater than the length of the slot.

22. The method according to claim 19, wherein the clear width of the cutout, measured in the longitudinal direction of the slot, is only a little larger than the width of the extension of the labial leg of the dip.

23. A kit comprising a bracket for use in orthodontia, having
a base;
a support arranged on the base;
an occlusal wall with at least one occlusal ligature wing extending from the support;
a gingival wall with at least one gingival ligature wing extending from the support;
a slot separating the occlusal wall from the gingival wall and extending continuously in the mesial-to-distal direction;
and a passage which extends continuously through the support in the gingival-to-occlusal direction;
as well as two different resilient clips which can be exchanged one against the other and which have one labial leg and one lingual leg that are connected one with the other by a section on the occlusal or gingival side, where the lingual leg can be introduced into the passage and can be moved therein only in gingival-occlusal direction between a closed position in which the labial leg extends into a cutout in the gingival wall or in the occlusal wall, which is provided with a stop for the labial leg at least in the labial direction,
and an open position of the clip in which the tip of the labial leg is positioned above the occlusal wall or above the gingival wall, respectively, and where the labial leg at least of a first clip of the two different resilient clips has a wing that extends in distal direction and a wing that extends in mesial direction,
with the particularity that in the closed position of the first clip a gingival or occlusal extension, respectively, of the labial leg is in contact with the labial stop, or nearly in contact with the labial stop even when the slot is empty, whereas the labial leg of a second clip of the two different resilient clips is spaced a greater distance from the labial stop, in the closed position, than the extension of the labial leg of the first clip when the slot is empty, a labial edge of the cutout has two straight sections that extend at an angle of more than 180° one relative to the other.

24. The kit as defined in claim 23, wherein the labial leg of the second clip is in contact with a lingual stop, provided between the labial stop and the passage, or is nearly in contact with that lingual stop in the closed position of the clip.

25. The kit as defined in claim 24, wherein the labial leg of the second slip is contacting the lingual stop at a pre-stress.

26. The kit as defined in claim 23, wherein when the slot is otherwise empty, the labial leg of the second clip is spaced by no more than 0.5 mm from the lingual bottom of the slot.

27. The kit as defined in claim 23, wherein the labial leg of the second clip has two wings one extending in mesial direction and the other one extending in distal direction.

28. The kit as defined in claim 23, wherein the labial leg of the first clip has two wings, which extend one in the mesial direction and one in the distal direction and which are positioned above the slot or in the labial region of the slot in the closed position of the first clip.

29. The kit as defined in claim 28, wherein the wings do not extend into the cutout.

30. The kit as defined in claim 23, wherein the labial leg of the first clip is spaced from the bottom of the slot by at least 0.025 inches (corresponding to 0.64 mm) in the closed position of the clip and with the slot in empty condition.

* * * * *